United States Patent [19]

Rowsell et al.

[11] 4,034,109

[45] July 5, 1977

[54] COMPOUNDS HAVING A PHYSIOLOGICAL COOLING EFFECT AND COMPOSITIONS CONTAINING THEM

[75] Inventors: David G. Rowsell, Staines; Roger Hems, Maidenhead, both of England

[73] Assignee: Wilkinson Sword Limited, England

[22] Filed: July 20, 1973

[21] Appl. No.: 381,098

[30] Foreign Application Priority Data

Jan. 18, 1973 United Kingdom ............... 2686/73

[52] U.S. Cl. ............................ 424/311; 424/248.5; 424/267; 424/321

[51] Int. Cl.² ................. A61K 31/22; A61K 31/18

[58] Field of Search ..................... 424/321, 16, 311

[56] References Cited

UNITED STATES PATENTS

| | | | |
|---|---|---|---|
| 2,955,980 | 10/1960 | Goodhue et al. | 424/321 |
| 3,644,653 | 2/1972 | Tcheiltcheff | 424/358 |

OTHER PUBLICATIONS

Remington's Pharmaceutical Sciences, 1965, 13th Edition, p. 855.
Wilson et al, Textbook of Organic Medicinal and Pharmaceutical Chemistry, 4th Edition, 1962, pp. 111–112.
Chemical Abstracts, 7th Cumulative Index, (1962–1966), vol. 56–65, pp. 13780s–13782s.
Chemical Abstracts, 8th Edition Cumulative Index, (1967–1971), vols. 66–75, pp. 18623s–18627s.

*Primary Examiner*—Norman A. Drezin
*Attorney, Agent, or Firm*—Leydig, Voit, Osann, Mayer & Holt, Ltd.

[57] ABSTRACT

Compositions are disclosed having a physiological cooling action on the skin. The compositions contain as the active ingredient certain acyclic sulphonamides and sulphinamides.

1 Claim, No Drawings

COMPOUNDS HAVING A PHYSIOLOGICAL COOLING EFFECT AND COMPOSITIONS CONTAINING THEM

FIELD OF INVENTION

This invention relates to topical and other compositions having a physiological cooling effect on the skin and on the mucous membranes of the body, particularly the nose, mouth, throat and gastrointestinal tract.

BACKGROUND OF THE INVENTION

Menthol is well known for its physiological cooling effect on the skin and mucous membranes of the mouth and has been extensively used as a flavouring agent (methol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

Other compounds have been mentioned in the art as having a physiological cooling effect e.g. 2,4,6-trimethyl-4-heptanol (Parfums-Cosmetiques-Savons, May 1956, pages 17-20) and N,N-diethyl-2-ethylbutanamide (French Pat. No. 1,572,332).

The object of the present invention is to provide other compounds having a physiological cooling effect similar to that obtained with menthol but without its attendant disadvantages.

It is a further object of the invention to provide ingestible, topical and other compositions containing such compounds in an amount to provide a physiological cooling effect when such compositions are used in or by the human body.

It is a further object to provide a method of stimulating the cold receptors of the body using agents other than methanol.

SUMMARY OF INVENTION

According to the invention we have found a group of acyclic sulphonamides and sulphinamides which are capable of stimulating the cold receptors of the nervous system of the body.

DETAILED DESCRIPTION OF INVENTION

The compounds having this physiological cooling effect and used in accordance with this invention are acyclic sulphonamides and sulphinamides of the formula:

$$RSO_xNR_1R_2$$

where
- R is a secondary or tertiary alkyl group of from 5–12 carbon atoms;
- $R_1$ and $R_2$, when taken separately, each represent hydrogen or a $C_1$–$C_{12}$ alkyl or hydroxyalkyl group and together provide a total of no more than 12 carbon atoms, with the proviso that when $R_1$ is hydrogen, $R_2$ may also be an alkylcarboxyalkyl group of up to 12 carbon atoms; and
- $R_1$ and $R_2$ when taken together, represent an alkylene group of up to 6 carbon atoms the ends of which are joined to the nitrogen atom thereby to form a nitrogen heterocycle, the carbon atom chain of which may optionally be interrupted by oxygen; and
- $x$ is 1 or 2,
- R, $R_1$ and $R_2$ together providing a total of from 6–18 carbon atoms.

In accordance with this invention, therefore, we provide compositions and articles capable of imparting a physiological cooling effect to the skin and mucous membranes of the body, when brought into contact therewith, such compositions comprising as an active constituent an acyclic sulphonamide or sulphinamide of the above formula.

The preferred acyclic sulphonamides and sulphinamides used in the compositions of this invention are those in which R is a tertiary alkyl group containing from 6–10 carbon atoms, and one of $R_1$ and $R_2$ is a $C_1$–$C_6$ alkyl radical and the other is hydrogen or $C_1$–$C_6$ alkyl, the total number of carbon atoms contributed by R, $R_1$ and $R_2$ being in the range 10–16.

Also preferred are the sulphinamides i.e. compounds of the above formula where $x$ is 1.

Typical compounds which may be used in the compositions of this invention include N-n-hexyl-2-methylpent-3-yl sulphinamide, N,N-diethyl-3-methylpent-3-yl sulphinamide, N-isopropyl hex-3-yl sulphinamide, N-n-octyl-2-methylpent-4-yl sulphinamide, N,N-diethyl-3-methylpent-3-yl sulphonamide, N,N-diethyl oct-2-yl sulphinamide, and N-n-hexyl-2-methylpent-3-yl sulphonamide.

The cooling sensation created by the compounds used in this invention on the skin and mucous membranes, for example, in the mouth, varies in intensity and longevity from compound to compound. An indication of the relative activity of various compounds used according to this invention is given below in the Table. In order to obtain these results, sample quantities of the compounds were tested by a panel of observers who were asked to assess the strength of the cooling effect produced and give it a rating according to an arbitrary scale. The results are reproduced below, the more stars the greater the effect.

TABLE

| x  | R                | $R_1$      | $R_2$              | Cooling Effect. |
|----|------------------|------------|--------------------|-----------------|
| 1  | 3-methylpent-3-yl | ethyl      | ethyl              | * * *           |
| "  | 3-methylpent-3-yl | H          | n-hexyl            | * *             |
| "  | 2-methylhept-4-yl |            | —$CH_2CH_2CH_2CH_2$— | * *         |
| "  | 2-methylpent-4-yl | isopropyl  | isopropyl          | *               |
| "  | hex-3-yl          | "          | "                  | *               |
| "  | "                 | H          | "                  | *               |
| "  | pent-3-yl         | isopropyl  | "                  | *               |

TABLE-continued

| x | R | R₁ | R₂ | Cooling Effect. |
|---|---|----|----|-----------------|
| 2 | 3-methylpent-3-yl | ethyl | ethyl | * |
| 1 | 2-methylpent-4-yl | H | n-butyl | * |
| " | 2-methylpent-3-yl | H | n-hexyl | * |
| " | pent-3-yl | isopropyl | isopropyl | * |
| " | " | H | n-octyl | * |
| " | 2-methyloct-3-yl | methyl | methyl | * |
| " | " | —CH₂CH₂OCH₂CH₂— | | * |
| " | 2,8-dimethylnon-5-yl | ethyl | ethyl | * |
| " | " | methyl | β-hydroxyethyl | * |
| 1 | 2-methylpent-4-yl | H | n-octyl | * |
| " | 2-methylpent-3-yl | n-propyl | n-propyl | * |
| " | hex-3-yl | H | n-octyl | * |
| " | pent-3-yl | H | " | * |
| " | oct-2-yl | ethyl | ethyl | * |
| " | " | H | " | * |
| 2 | 2-methylpent-3-yl | H | n-hexyl | * |
| " | hex-3-yl | H | n-octyl | * |
| " | pent-3-yl | ethyl | ethyl | * |

Certain compounds used in this invention exhibit optical isomerisation and, depending on the starting materials and the methods used, the compounds used in this invention may be isomerically pure, i.e. consisting of one optical isomer, or they may be mixtures of optical isomers. In most cases the compounds will be used in an isomer mixture, but with certain compounds there may be a difference in cooling effect as between isomers, for example, as between d- and l-forms, and in such cases one or other isomer may be preferred.

The sulphonamides and sulphinamides used in this invention may be readily prepared by conventional methods, such as by the reaction of the corresponding acid chloride with ammonia or with the appropriate mono- or di-substituted amine. The reaction proceeds smoothly at room temperature.

The compounds of this invention find utility as additives for a wide variety of compositions and articles which in use come in contact with, are applied to or consumed by the body i.e., as additives for consumer products which are prepared for a human body use, but more especially in compositions for topical application to the human body. Typical topical compositions into which the compounds of the invention can be incorporated to give a pleasant cooling effect on the skin include toilet compositions, e.g. toilet water, after-shave lotions, talcum powder, and other lotions, liniments, oils and ointment applied to the external surfaces of the human body, whether for medical or other reasons. The compounds of the invention may also be incorporated in compositions applied to, or which, in normal usage, come in contact with, internal mucous membranes of the body, such as those of the nose, mouth, or throat, whether by direct or indirection application or inhalation, e.g. nasal and throat sprays, dentifrice, mouthwash and gargle compositions. Such compositions being regarded herein as "topical" i.e. as opposed to "ingestible". The compounds may also be used to impregnate toilet articles such as cleansing tissues and toothpicks.

A further class of compositions included within the scope of this invention are tobacco and associated articles e.g. pipe and cigarette filters, especially filter tips for cigarettes.

Because of the cooling effect created in the mouth and in the gastrointestinal tract, the compounds of the invention may also find utility in foodstuffs and beverages. However, because of a bitter taste such usage is not preferred, although there may be compositions where the bitter flavour, plus a cooling effect may be desirable.

The compositions of this invention will contain an amount of the cold receptor stimulant sufficient to stimulate the cold receptors in the areas of the skin or mucous membrane with which the compositions come into contact and thereby promote the desired cold sensation. Since the degree and longevity of cooling sensation varies from compound to compound the quantity of stimulant used in each composition will vary widely. As a guide, it may be said that, with the more active compounds of the invention, a significant cooling sensation is achieved upon application to the skin of as little as 0.05 ml of a 1.0 weight percent solution of the active ingredient in ethanol. For the less active compounds a significant cooling effect is achieved only with more concentrated solutions, e.g. 5% by weight or more of the active ingredient.

In formulating the compositions of this invention the cold receptor stimulant will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the stimulant include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and halohydrocarbons used as aerosol propellants; gums and natural or synthetic resins.

Because of the cooling sensation imparted to the skin, a major utility of the compounds of this invention will be in a wide range of toilet preparations and toilet articles. The particular preparations discussed below are to be taken as exemplary.

A major utility will be in after shave lotions, toilet water etc., where the compound will be used in alcoholic or aqueous alcoholic solution, such solutions usually also containing a perfume or mild antiseptic or both. The amount of compound added to the formulation will usually be in the range 1.0 to 10.0% by weight based on the total composition.

Another field of utility will be in soaps, shampoos, bath oils etc. where the compounds of the invention will be used in combination with an oil or fat or a natural or synthetic surfactant e.g. a fatty acid salt or a lauroylsulphate salt, the composition usually also containing an essential oil or perfume. The range of soap compositions will include soap of all kinds e.g. toilet soaps, shaving soaps, shaving foams etc. Usually the compound will be added to the formulation in amount of from 1 to 10% by weight.

A further class of tiolet composition into which the compounds of this invention may be incorporated includes cosmetic creams and emollients, such creams and emollients usually comprising a base emulsion and optionally a range of ingredients such as wax, preservative, perfume, antiseptics, astringents, pigments etc. Also included within this class are lipstick and solid cologne compositions such compositions usually comprising an oil and wax base into which the compound can be incorporated along with the conventional ingredients, i.e. pigments, perfumes etc. Once again the formulation of such compositions, apart from the incorporation of the active compound, usually in an amount of from 0.5–10%, by weight is conventional. Compositions according to the invention are illustrated by the following Examples, all percentages are by weight.

EXAMPLE 1

After Shave Lotion

An after shave lotion was prepared according to the following recipe by dissolution of the ingredients in the liquid and cooling and filtering:

| | |
|---|---|
| Denatured Ethanol | 75% |
| Diethylphthalate | 1.0% |
| Propylene glycol | 1.0% |
| Lactic acid | 1.0% |
| Perfume | 3.0% |
| Water | to 100% |

Into a sample of the base lotion was added 2.0% by weight based on the total composition of N,N-diethyl-3-methylpent-3-yl sulphinamide.

When applied to the face a noticeable cooling effect became apparent after a short interval of time.

EXAMPLE 2

Toilet Water

A toilet water was prepared according to the following recipe:

| | |
|---|---|
| Denatured Ethanol | 75.0% |
| Perfume | 5.0% |
| Water | to 100% |

To the recipe was added 3.0%, based on the total composition, of N-n-hexyl 2-methylpent-3-yl sulphinamide.

As with the after shave lotion, a cooling effect was noticeable on the skin well after the termination of any cooling effect attributable to the evaporation of the alcoholic carrier.

EXAMPLE 3

Antiseptic Ointment

An ointment was prepared according to the following formulation:

| | |
|---|---|
| Cetyltrimethyl ammonium bromide | 4.0% |
| Cetyl alcohol | 6.0% |
| Stearyl Alcohol | 6.0% |

-continued

| | |
|---|---|
| White Paraffin | 14.0% |
| Mineral Oil | 21.0% |
| Water | to 100% |

The ingredients were mixed, warmed to 40° C and emulsified in a high speed blender. Added to the mixture during blending was 2.5% of N-isopropyl hex-3-yl sulphinamide.

The final ointment when applied to the skin gave rise to a noticeable cooling effect.

EXAMPLE 4

Antipruritic Ointment

The following ingredients were warmed together to form a homogeneous melt:

| | |
|---|---|
| Methyl salicylate | 50.0% |
| White Beeswax | 25.0% |
| Anhydrous Lanolin | 25.0% |

To the melt was added 3.0% of N,N-diethyl-3-methylpent-3-yl sulphonamide, and the mixture allowed to solidify. A soft ointment resulted having a soothing effect on the skin accompanied by a noticeable cooling effect.

EXAMPLE 5

Cleansing Tissue

A cleansing liquid was prepared having the following formulation:

| | |
|---|---|
| Triethanolamine Lauryl sulphate | 1.0% |
| Glycerol | 2.0% |
| Perfume | .95% |
| Water | to 100% |

To this liquid was added 3.0% of N,N-diisopropyl hex-3-yl sulphinamide. A paper tissue was then soaked in this liquid.

When the impregnated tissue is used to wipe the skin a fresh cool sensation is noticed after a short interval.

EXAMPLE 6

Toothpaste

The following ingredients were mixed in a blender:

| | |
|---|---|
| Dicalcium Phosphate Dihydrate | 40% |
| Sodium Lauryl Sarcosinate | 1.5% |
| Glycerol | 30% |
| Sodium Carboxymethyl Cellulose | 1.5% |
| Saccharin Sodium | 0.2% |
| Sodium Benzoate | 0.2% |
| Water | 26.6% |

Shortly before completion of the blending operation 3.0% by weight of N,N-diethylpent-3-yl sulphonamide was added to the blender.

When applied as a toothpaste, a cooling effect is noticed in the mouth.

EXAMPLE 7

Aerosol Shaving Soap

An aerosol shaving soap composition was formulated according to the following recipe:

| Stearic Acid | 6.3% |
|---|---|
| Lauric Acid | 2.7% |
| Triethanolamine | 4.6% |
| Sodium Carboxymethyl Cellulose | 0.1% |
| Sorbitol | 5.0% |
| Water | to 100% |
| Perfume | 0.5% |

The composition was prepared by fusing the acids in water, adding the triethanolamine, cooling and adding the other constituents. To the mixture was then added 2% N-n-octyl hex-3-yl sulphinamide. The composition was then packaged in an aerosol dispenser under pressure of a butane propellant.

When used in shaving a fresh cool sensation was distinctly noticeable on the face.

EXAMPLE 8

Deodorant Composition

A deodorant composition suitable for formulation and dispensing as an aerosol under pressure of a suitable propellant was formulated according to the following recipe:

| Denatured ethanol | 96.9% |
|---|---|
| Hexachlorophene | 2.0% |
| Isopropyl myristate | 1.0% |
| Perfume | 0.1% |

To the composition was added 6% by weight of N,N-diethyl 3-methylpent-3-yl sulphonamide. Application of the final composition gave rise to a definite cooling sensation on the skin.

EXAMPLE 9

Hair Shampoo

Sodium lauryl ether sulphate, 10 g, was dispersed in 90 g water in a high speed mill. To the dispersion was added 6.0% by weight of N,N-di-n-propyl 2-methylpent-3-yl sulphinamide. When the hair is washed using the shampoo a fresh, cool sensation is noticed on the scalp.

EXAMPLE 10

Solid Cologne

A solid cologne was formulated according to the following recipe:

| Denatured ethanol | 74.5% |
|---|---|
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 6.0% of N-ethyl oct-2-yl sulphinamide, and the mixture then allowed to solidify into a waxy cake.

When applied to the forehead a distinct cooling effect is noticeable.

EXAMPLE 11

Mouthwash

A concentrated mouthwash composition was prepared according to the following recipe:

| Ethanol | 3.0% |
|---|---|
| Borax | 2.0% |
| Sodium Bicarbonate | 1.0% |
| Glycerol | 10.0% |
| Flavourant | 0.4% |
| Thymol | 0.03% |
| Water | to 100% |

To the composition was added 0.2% of N-n-hexyl 3-methylpent-3-yl sulphinamide.

When diluted with approximately 10 times its own volume of water and used to rinse the mouth a cooling effect is obtained in the mouth.

EXAMPLE 12

Hydrophilic Ointment

A hydrophilic ointment was prepared having the following formulation:

| Propylene Glycol | 12% |
|---|---|
| 1-Octadecanol | 25% |
| White soft paraffin | 25% |
| Sodium lauryl sulphate | 1% |
| Water | to 100% |

The sodium lauryl sulphate was added to the water and heated to 60° C. The paraffin was melted by heating to 60° C and was then added to the sodium lauryl sulphate mixture with stirring. Propylene glycol and 1-octadecanol were then added to this mixture.

To the resultant mixture was added 3% of N,N-diethyl 3-methylpent-3-yl sulphinamide. The final ointment when applied to the skin gave rise to a marked cooling effect.

EXAMPLE 13

Liniment

A liniment was prepared according to the following formulation:

| Methyl salicylate | 25% |
|---|---|
| Eucalyptus Oil | 10% |
| Arachis Oil | to 100% |

To the composition was added 6% of N,N-diethyl 3-methylpent-3-yl sulphonamide.

When the final composition was applied to the skin a clearly noticeable cooling effect became apparent after a short interval of time.

EXAMPLE 14

Cigarette Tobacco

A proprietary brand of cigarette tobacco was impregnated with N-methyl-N-(β-hydroxyethyl)-2,8-dimethylnon-5-yl sulphinamide and was rolled into cigarettes each containing approximately 0.005 gm of active compound. Smoking the impregnated cigarettes produced a cool effect in the mouth characteristic of mentholated cigarettes.

A similar effect is noticed when smoking a proprietary brand of tipped cigarette, the coolant being used to impregnate the filter tip rather than the tobacco.

The above Examples illustrate the range of compounds and the range of compositions included in the invention. However, they are not to be taken as limiting the scope of the invention in any way. Other compounds within the general formula will be equally suitable for use in the compositions of Examples 1–14 and the physiological effect obtained with the compounds of the invention will recommend their use in a wide variety of other compositions where the cooling effect will be of value.

We claim:

1. A method of stimulating the cold receptors of the nervous system of the surface tissues of the human body, which comprises bringing into contact with said tissues an effective amount of a cold receptor stimulating acyclic sulphonamide or sulphinamide of the formula:

$$RSO_xNR_1R_2$$

where
R is a secondary or tertiary alkyl group containing from 5–12 carbon atoms;
$R_1$ and $R_2$, when taken separately, are each hydrogen, $C_1$–$C_{12}$ alkyl or $C_1$–$C_{12}$ hydroxyalkyl, and together provide a total of no more than 12 carbon atoms, with the proviso that when $R_1$ is hydrogen $R_2$ may also be alkylcarboxyalkyl of up to 12 carbon atoms; and $x$ is an integer of from 1–2 inclusive,
R, $R_1$ and $R_2$ together providing a total of from 6–18 carbon atoms.

* * * * *